(12) United States Patent
Daniels et al.

(10) Patent No.: US 7,794,503 B2
(45) Date of Patent: Sep. 14, 2010

(54) TRIALING SYSTEM AND METHOD FOR MODULAR HIP JOINT REPLACEMENT SYSTEM

(75) Inventors: David W. Daniels, Warsaw, IN (US); Kimberly A. Dwyer, Fort Wayne, IN (US); David Mattingly, Weston, MA (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 11/810,608

(22) Filed: Jun. 6, 2007

(65) Prior Publication Data

US 2007/0244566 A1    Oct. 18, 2007

Related U.S. Application Data

(63) Continuation of application No. 10/327,488, filed on Dec. 20, 2002, now Pat. No. 7,235,106.

(51) Int. Cl.
    *A61F 2/32* (2006.01)
(52) U.S. Cl. .............. 623/22.11; 623/22.42; 623/23.21; 623/23.44; 623/23.46
(58) Field of Classification Search .............. 623/20.34, 623/20.36, 22.11, 22.41, 22.42, 22.44, 22.45, 623/22.46, 23.15, 23.21, 23.22, 23.23, 23.46, 623/23.47
See application file for complete search history.

(56) References Cited

U.S. PATENT DOCUMENTS

| | | | |
|---|---|---|---|
| 2,492,249 | A | 12/1949 | Willard et al. |
| 3,067,740 | A | 9/1959 | Harboush |
| 3,271,868 | A | 9/1966 | Kuntscher et al. |
| 3,801,989 | A | 4/1974 | McKee |
| 3,810,312 | A | 5/1974 | Carson |
| 4,051,559 | A | 10/1977 | Pifferi |
| 4,131,998 | A | 1/1979 | Spears |
| 4,335,715 | A | 6/1982 | Kirkley |
| 4,517,969 | A | 5/1985 | Halcomb, III et al. |
| 4,608,055 | A | 8/1986 | Morrey et al. |

(Continued)

FOREIGN PATENT DOCUMENTS

AU    2003266447    7/2004

(Continued)

OTHER PUBLICATIONS

European Search Report for European Application No. 03257810.6, Apr. 5, 2004 (3 pages).

(Continued)

*Primary Examiner*—David H Willse
*Assistant Examiner*—Javier G Blanco
(74) *Attorney, Agent, or Firm*—Maginot, Moore & Beck

(57) ABSTRACT

A system and method for trialing a modular hip replacement system (10) permits evaluation and replication of the anatomic anteversion rotational angle of the femur. A distal stem component (18) of the hip replacement system (10) includes a proximal portion (34) having a locator feature (35) that is externally accessible when the stem component is mounted within the femur. A proximal trial body assembly (60) is mounted on the proximal portion (34) of the distal stem component (18) to permit rotation of a trial neck component (62). The trial neck component (62) also includes a locator feature (126) that can be externally referenced to determine the anteversion angle.

15 Claims, 7 Drawing Sheets

U.S. PATENT DOCUMENTS

| | | |
|---|---|---|
| 4,658,808 A | 4/1987 | Link |
| 4,676,797 A | 6/1987 | Anapliotis et al. |
| 4,716,894 A | 1/1988 | Lazzeri et al. |
| 4,917,530 A | 4/1990 | Engelhardt et al. |
| 4,938,762 A | 7/1990 | Wehrli |
| 4,959,066 A | 9/1990 | Dunn et al. |
| 4,969,911 A | 11/1990 | Greene et al. |
| 5,002,578 A | 3/1991 | Luman |
| 5,002,581 A | 3/1991 | Paxson et al. |
| 5,064,427 A | 11/1991 | Burkinshaw |
| 5,100,407 A | 3/1992 | Conrad et al. |
| 5,133,760 A | 7/1992 | Petersen et al. |
| 5,135,529 A | 8/1992 | Paxson et al. |
| 5,197,989 A | 3/1993 | Hinckfuss et al. |
| 5,201,882 A | 4/1993 | Paxson |
| 5,314,492 A | 5/1994 | Hamilton et al. |
| 5,364,401 A | 11/1994 | Ferrante et al. |
| 5,370,706 A | 12/1994 | Bolesky et al. |
| 5,476,466 A | 12/1995 | Barrette et al. |
| 5,507,824 A | 4/1996 | Lennox |
| 5,507,830 A | 4/1996 | DeMane et al. |
| 5,514,136 A | 5/1996 | Richelsoph |
| 5,601,567 A | 2/1997 | Swajger et al. |
| 5,607,431 A | 3/1997 | Dudasik et al. |
| 5,645,607 A | 7/1997 | Hickey |
| 5,653,765 A | 8/1997 | McTighe et al. |
| 5,658,349 A | 8/1997 | Brooks et al. |
| 5,674,225 A | 10/1997 | Müller |
| 5,700,268 A | 12/1997 | Bertin |
| 5,725,592 A | 3/1998 | White et al. |
| 5,728,128 A | 3/1998 | Crickenberget et al. |
| 5,766,261 A | 6/1998 | Neal et al. |
| 5,776,200 A | 7/1998 | Johnson et al. |
| 5,792,143 A | 8/1998 | Samuelson et al. |
| 5,810,829 A | 9/1998 | Elliott et al. |
| 5,810,830 A | 9/1998 | Noble et al. |
| 5,824,068 A | 10/1998 | Bugge |
| 5,849,015 A | 12/1998 | Haywood et al. |
| 5,858,020 A | 1/1999 | Johnson et al. |
| 5,860,969 A | 1/1999 | White et al. |
| 5,876,459 A | 3/1999 | Powell |
| 5,879,391 A | 3/1999 | Slamin |
| 5,885,299 A | 3/1999 | Winslow et al. |
| 5,888,245 A | 3/1999 | Meulink et al. |
| 5,902,339 A | 5/1999 | Keller |
| 5,906,644 A | 5/1999 | Powell |
| 5,919,195 A | 7/1999 | Wilson et al. |
| 5,935,172 A | 8/1999 | Ochoa et al. |
| 5,951,564 A | 9/1999 | Schroder et al. |
| 5,951,606 A | 9/1999 | Burke |
| 5,976,147 A | 11/1999 | LaSalle et al. |
| 5,976,188 A | 11/1999 | Dextradeur et al. |
| 5,989,259 A | 11/1999 | Penenberg et al. |
| 5,993,455 A | 11/1999 | Noble |
| 6,027,507 A | 2/2000 | Anderson et al. |
| 6,045,556 A | 4/2000 | Cohen |
| 6,071,311 A | 6/2000 | O'Neil et al. |
| 6,080,162 A | 6/2000 | Dye et al. |
| 6,097,978 A | 8/2000 | Demarais et al. |
| 6,102,950 A | 8/2000 | Vaccaro |
| 6,102,956 A | 8/2000 | Kranz |
| 6,110,179 A | 8/2000 | Flivik et al. |
| 6,113,605 A | 9/2000 | Storer |
| 6,117,138 A | 9/2000 | Burrows et al. |
| 6,126,694 A | 10/2000 | Gray, Jr. |
| 6,136,035 A | 10/2000 | Lob et al. |
| 6,165,177 A | 12/2000 | Wilson et al. |
| 6,179,877 B1 | 1/2001 | Burke |
| 6,193,724 B1 | 2/2001 | Chan |
| 6,193,759 B1 | 2/2001 | Rio et al. |
| 6,197,065 B1 | 3/2001 | Martin et al. |
| 6,206,844 B1 | 3/2001 | Reichel et al. |
| 6,206,884 B1 | 3/2001 | Masini |
| 6,224,605 B1 | 5/2001 | Anderson et al. |
| 6,238,435 B1 | 5/2001 | Meulink et al. |
| 6,258,095 B1 | 7/2001 | Lombardo et al. |
| 6,258,097 B1 | 7/2001 | Cook et al. |
| 6,277,123 B1 | 8/2001 | Maroney et al. |
| 6,319,286 B1 | 11/2001 | Fernandez et al. |
| 6,330,845 B1 | 12/2001 | Meulink |
| 6,332,886 B1 | 12/2001 | Green et al. |
| 6,355,068 B1 | 3/2002 | Doubler et al. |
| 6,361,563 B2 | 3/2002 | Terrill-Grisoni et al. |
| 6,432,110 B1 | 8/2002 | Richelsoph |
| 7,235,106 B2 | 6/2007 | Daniels et al. |
| 2001/0001121 A1 | 5/2001 | Lombardo et al. |
| 2001/0007957 A1 | 7/2001 | Martin et al. |
| 2001/0053935 A1 | 12/2001 | Hartdegen et al. |
| 2007/0244566 A1 | 10/2007 | Daniels et al. |

FOREIGN PATENT DOCUMENTS

| | | |
|---|---|---|
| EP | 0 381 893 | 8/1990 |
| EP | 0 677 281 | 10/1995 |
| EP | 0 824 013 | 2/1998 |
| EP | 1 004 283 | 5/2000 |
| EP | 1 022 001 | 7/2000 |
| EP | 1099427 | 5/2001 |
| EP | 1 234 558 | 8/2002 |
| EP | 1437103 | 7/2004 |
| FR | 2 416 002 | 8/1979 |
| FR | 2 492 249 | 4/1982 |
| FR | 2 684 287 | 6/1993 |
| FR | 2 705 558 | 12/1994 |
| FR | 2735971 | 1/1997 |
| FR | 2735971 A1 * | 1/1997 |
| JP | 2004202234 | 7/2004 |
| WO | WO 96/15739 | 5/1996 |
| WO | WO 02 17826 | 3/2002 |

OTHER PUBLICATIONS

European Search Report for European Application No. 03257813.0, May 11, 2004 (2 pages).

European Search Report for European Application No. 03257816.3, May 18, 2004 (2 pages).

Zimmer brochure entitled "ZMR Revision Taper Hip Prosthesis"; Copyright 1999 Zimmer, Inc.; 26 pages.

AcuMatch brochure entitled "AcuMatch M-Series Modular Femoral Stem, Operative Technique Draft"; Copyright 2001 Exactech, Inc.; 14 pages.

Stryker brochure entitled "Restoration Modular Revision Hip System, Surgical Protocol"; For purposes of this patent application only, this Stryker brochure depicts a prosthetic device publicly available at least as earlier as Dec. 19, 2002; 22 pages.

Biomet brochure entitled "Mallory-Head Modular Calcar, Modular Calcar Revision System"; For purposes of this patent application only, this Biomet brochure depicts a prosthetic device publicly available at least as earlier as Dec. 19, 2002; 20 pages.

LINK brochure entitled "Surgical Technique with the MP Hip Stem for Revision of a Failed Femoral Hip Stem"; For purposes of this patent application only, this LINK brochure depicts a prosthetic device publicly available at least as earlier as Dec. 19, 2002; 12 pages.

* cited by examiner

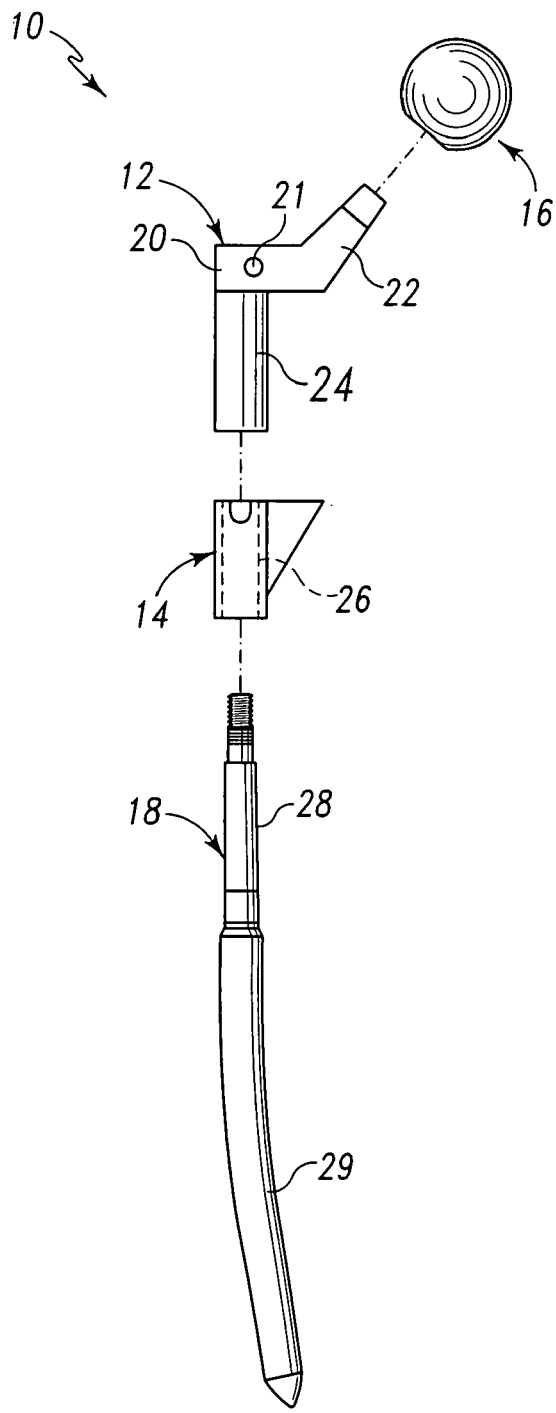
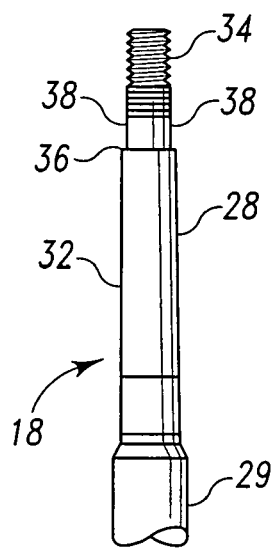
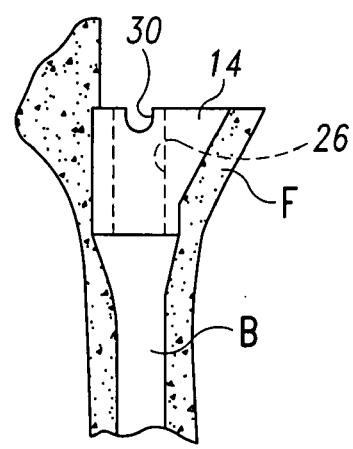
Fig. 1
Fig. 2
Fig. 3

TRIALING SYSTEM AND METHOD FOR MODULAR HIP JOINT REPLACEMENT SYSTEM

This application is a continuation of application Ser. No. 10/327,488, filed on Dec. 20, 2002 (now U.S. Pat. No. 7,235,106). The disclosure of the above-identified published patent application is hereby totally incorporated by reference in its entirety.

CROSS-REFERENCE TO RELATED APPLICATIONS

Cross reference is made to the following applications: U.S. application Ser. No. 10/327,187, filed on Dec. 20, 2002 which is entitled "ADJUSTABLE BIOMECHANICAL TEMPLATING & RESECTION INSTRUMENT AND ASSOCIATED METHOD", U.S. application Ser. No. 10/327,196, filed on Dec. 20, 2002 (now U.S. Pat. No. 7,022,141) which is entitled "ALIGNMENT DEVICE FOR MODULAR IMPLANTS AND METHOD", and U.S. application Ser. No. 10/327,527, filed on Dec. 20, 2002 which is entitled "INSTRUMENT AND ASSOCIATED METHOD OF TRIALING FOR MODULAR HIP STEMS". The disclosures of each of the above-identified patent applications and patent(s) are hereby totally incorporated by reference in their entirety.

TECHNICAL FIELD OF THE INVENTION

The present invention relates generally to a system and method for trialing components of a modular hip prosthesis, and particularly to a system and method capable of gauging the degree of anteversion of the femur.

BACKGROUND OF THE INVENTION

During the lifetime of a patient, it may be necessary to perform a joint replacement procedure on the patient as a result of, for example, disease or trauma. The joint replacement procedure, or joint arthroplasty, may involve the use of a prosthesis which is implanted into one of the patient's bones. In the case of a hip replacement procedure, a femoral prosthesis is implanted into the patient's thigh bone or femur. One type of early femoral prosthesis was typically constructed as a one-piece structure having an upper portion which includes a spherically-shaped head which bears against the patient's pelvis or acetabulum, along with an elongated intramedullary stem which is utilized to secure the femoral component to the patient's femur. In order to secure the prosthesis to the patient's femur, the medullary canal of the patient's femur is first surgically prepared (e.g. reamed and/or broached) such that the intramedullary stem of the femoral prosthesis may be subsequently implanted therein. The femoral prosthesis may be press fit into the medullary canal or, in the alternative, bone cement may be utilized to secure the femoral prosthesis within the medullary canal.

During performance of a joint replacement procedure, it is generally important to provide the orthopaedic surgeon with a certain degree of flexibility in the selection of a prosthesis. In particular, the anatomy of the bone into which the prosthesis is to be implanted may vary somewhat from patient to patient. For example, in the case of a femoral prosthesis, the patient's femur may be relatively long or relatively short thereby requiring use of a femoral prosthesis which includes a stem that is relatively long or short, respectively. Moreover, in certain cases, such as when use of a relatively long stem length is required, the stem must also be bowed in order to conform to the anatomy of the patient's femur.

Such a need for prostheses of varying shapes and sizes can create a number of problems in regard to use of a one-piece prosthesis. For example, a hospital or surgery center must maintain a relatively large inventory of prostheses in order to have the requisite mix of prostheses needed for certain situations such as trauma situations and revision surgery. Moreover, since the bow of the stem must conform to the bow of the intramedullary canal of the patient's femur, rotational positioning of the upper portion (i.e. proximal end) of the prosthesis is limited thereby rendering precise locating of the upper portion and hence the head of the prosthesis very difficult. In addition, since corresponding bones of the left and right side of a patient's anatomy (e.g. left and right femur) may bow in opposite directions, it is necessary to produce "left" and "right" variations of the prosthesis in order to provide anteversion of the bowed stem thereby further increasing the inventory of prostheses which must be maintained.

As a result of these and other drawbacks, a number of modular prostheses have been designed. As its name implies, a modular prosthesis is constructed in modular form so that the individual elements or features of the prosthesis can be selected to fit the needs of a given patient's anatomy. For example, modular prostheses have been designed which include a proximal neck component which can be assembled to any one of numerous distal stem components in order to create an assembly which fits the needs of a given patient's anatomy. Such a design allows the distal stem component to be selected and thereafter implanted in the patient's bone in a position which conforms to the patient's anatomy while also allowing for a limited degree of independent positioning of the proximal neck component relative to the patient's pelvis.

In another type of modular implant, three components (in addition to the head) are utilized: a distal stem component that is engaged within the femur, a proximal metaphyseal filling component, and an intermediate neck component that supports the head component on the distal stem component. The provision of three components has greatly increased the degree of flexibility in producing a total hip implant that most closely approximates the patient's skeletal anatomy and normal joint movement. One such system is the S-ROM® total hip system marketed by DePuy Orthopaedics, Inc. The S-ROM® total hip system offers neck and head components having different lengths, different lateral offsets of the neck relative to the stem, as well as different stem configurations.

In order to properly size the final implant, many systems utilize trial implants, commonly referred to as simply trials. Thus, in modular systems such as the S-ROM® instrument system, neck trials, proximal body trials, distal stem trials, head trials and sleeve trials can be provided. Each trial is provided in a number of sizes and geometries to give the surgeon a wide range of combination from which to choose. The trials afford the orthopaedic surgeon the opportunity to assess the fit and position of a final implant without having to complete the fixation. Like the implant systems itself, the trials are modular to reduce the inventory of components and the complexity of the trialing process.

Success of the hip replacement procedure depends in large part on the technical precision with which the final implant is inserted and the modular components oriented relative to each other. Current trialing systems have performed well in assessing implant size and gross orientation, relying primarily on laser marking, for example. However, there remains an unfulfilled need for a trialing system (as well as a modular implant system) that is able to accurately reproduce the anteversion angle of the femur. The anteversion angle is an angle of rotation between the ball end of the femur and the plane of the intramedullary canal of the bone. In the context of the modular implant, the anteversion angle is the relative angular rotation of the proximal neck component relative to the distal stem component. Proper rotational position, or anteversion angle, allows for accurate and stable reproduction of the mechanical orientation and function of the reconstructed hip joint.

For implants having a straight distal stem, the proper anteversion angle can be obtained by simply spinning the distal stem within the prepared bore in the femur. In a typical case, the surgeon can visually evaluate the orientation of the proximal body relative to the surrounding anatomy. If a trial is used the trial is removed and the final prosthesis is implanted as close to the trial position as possible. Sometimes, x-rays are used to verify the rotational alignment, while some systems rely upon external references to verify alignment.

The S-ROM® total hip system described above utilizes laser markings on the proximal end of the distal stem and on the proximal sleeve. These markings enable the surgeon to measure relative anteversion rotational alignment between the components. Since the sleeve has infinite anteversion it is not necessarily oriented relative to a bony landmark that can be used to define the anteversion angle. In fact, for simplicity, most current sleeves are oriented with the laser marking pointing directly laterally into the remaining available bone of the femur.

The problem of ensuring proper anteversion alignment is exacerbated where the modular system includes a curved distal stem. As explained above, where a long distal stem is utilized, it must be curved to follow the natural shape of the femur. Obviously, a curved stem means that the rotational alignment cannot be modified by simply rotating the stem within the prepared bore, since the bore itself is also curved. Monolithic, or one-piece stems must be offered with a predetermined anteversion angle, typically fifteen degrees. At present no modular implant or modular trial system is available that allows for accurate reproduction of the anteversion rotational orientation.

SUMMARY OF THE INVENTION

The present invention contemplates a method for trialing a modular hip joint replacement system to determine the anteversion rotational angle of the femoral component. In one embodiment, the method includes the steps of disposing a distal stem component within a prepared bore in the femur, in which the distal stem component is configured for substantially permanent fixation within the prepared bore. The distal stem component has a proximal portion defining a stem locator feature. Next, a proximal trial assembly is mounted on the proximal portion of the distal stem component. The trial assembly defines a bore therethrough for accessing the locator recess in the distal stem component. The proximal trial assembly includes a first component rotatable relative to the distal stem component about a longitudinal axis of the proximal portion of the distal stem component. This first component also defines a locator feature independent of the stem locator feature. Moreover, the first component includes a portion configured as a trial neck so that the first component can be manipulated relative to the distal stem component to determine an anteversion rotational angle for the femoral component of the hip joint.

The first component of the proximal trial assembly is rotated relative to the distal stem component, while the stem component maintains its rotational position within the femur. The surgeon manipulates the first component until the trial neck portion is oriented at an acceptable anteversion rotational angle relative to the femur. At this point, an alignment instrument can be used to reference the anteversion orientation of the trial neck portion relative to the femur. In particular, the instrument references the locator features in the relatively fixed distal stem portion and the rotated component of the proximal trial assembly.

The inventive method can contemplate using the instrument referenced to the anteversion orientation to form the final femoral implant. In particular, the instrument can be fixed at its position when it referenced the locator features. The instrument then serves as a gauge or template for positioning a proximal neck component of the joint replacement system at the appropriate anteversion orientation relative to the distal stem component.

In some embodiments, the distal stem component of the hip replacement system is fixed within the bone bore in a conventional manner. With these embodiments, the proximal trial body assembly is used to evaluate the anteversion rotational angle and then removed. The alignment instrument can be engaged to a proximal component of the replacement system and used to place the proximal component on the distal stem component. Since the alignment instrument operates as a gauge, the proximal component can only be mounted on the distal stem component at the measured anteversion rotational angle. Once the proximal component is properly positioned on the proximal end of the distal stem component, the instrument is disengaged from the proximal component and the final fixation of the implant system is accomplished.

In another embodiment, the distal stem component is not fixed within the bore. With this embodiment, once the anteversion rotational angle has been determined, the distal stem component can be removed from the femur and separately assembled with the remaining components of the hip replacement system.

The present invention is particularly useful where the distal stem component is long and curved to match the curvature of the femur. However, the same principles can be used with a straight stem component.

The methods of the invention can be employed where the hip replacement system includes a sleeve component. The method can thus be modified to include the step of disposing the sleeve component within the prepared bore such that the proximal end of the distal stem component extends through the sleeve. The features of the inventive system and method allow the trialing procedure to occur even with the sleeve component disposed within the femur. As with the distal stem component, the sleeve component can be substantially permanently fixed within the bone bore or can be removably disposed in the femur. In the preferred embodiment, the proximal body assembly can be rotationally indexed to the sleeve component within the bone bore.

The invention further contemplates a distal stem component for a modular hip joint replacement system that can be readily used in a trialing procedure. The distal stem component can include a curved bone engaging portion configured for fixation within a prepared bore in the femur. A proximal portion of the component defines an engagement portion configured for engaging a proximal modular component of the hip joint replacement system. Moreover, the proximal portion defines a locator feature that is disposed at a predetermined angular orientation relative to the plane of curvature of the bone engaging portion (or the femur itself). The locator feature is arranged on the proximal portion to be accessible from outside the femur and is usable to provide a remote indication of the spatial orientation of the bone engaging portion even when it is within the prepared bore of the femur.

In a preferred embodiment, the locator feature is elongated along an axis extending along the predetermined angular orientation. In a more specific embodiment, the locator feature is a substantially oval recess defined in the exposed end of the proximal portion of the distal stem component. Other recess configurations are contemplated provided they are not configured as a uniform body of rotation, such as a circle, hexagon, octagon, and the like. In other words, the locator feature must be capable of indexed engagement by the alignment instrument to provide a substantially infallible remote indication of the rotational orientation of the distal stem component relative to the bone. Preferably, the oval recess is arranged with its long axis substantially perpendicular to the plane of curvature of the bone engaging portion.

In certain embodiments of the invention, the engagement portion of the distal stem component includes threads. The threads can be used to engage a nut used to fix the proximal trial body assembly to the proximal end of the distal stem component when the proper anteversion rotational angle has been ascertained. In addition, the threads can be used as part of the final fixation of the modular hip replacement system.

The distal stem component can also include opposite flats defined at the proximal portion of the component. These opposite flats can engage complementary internal flats of a second component of the proximal trial body assembly to essentially rotationally lock the component to the distal stem component. Thus, this second component does not rotate relative to the distal stem portion once the proximal trial body assembly has been mounted on the stem component. The trial body assembly can include a third component that is configured to engage the sleeve component of the final implant assembly. This third component is mounted for rotation about the second component to facilitate integration of the proximal trial body assembly with the distal stem and sleeve components.

The distal stem component can form part of a trialing system for determining the anteversion rotational angle of the femoral component of a modular hip replacement system. The trialing system includes a proximal trial body assembly that includes a first component defining a first bore for receiving at least a portion of the proximal portion of the distal stem component for accessing the stem locator feature. The first component is rotatable relative to the distal stem component about a longitudinal axis of the proximal portion of the distal stem component. The first component can also define a trial locator feature independent of the stem locator feature that is also accessible from outside the prepared bore in the femur. As indicated above, the first component can also include a portion configured as a trial neck component for the modular hip replacement system.

The proximal trial body assembly also includes a second component defining a second bore configured for mounting the second component on the distal stem component with the proximal portion of the distal stem component extending through the bore. An interdigitating engagement is defined between the first and second components for fixing the first component to the second component after the first component has been rotated relative to the distal stem component. The interdigitating engagement can preferably be in the form of complementary radially splined surfaces. The interdigitating engagement can permit relative rotation between the two components while the anteversion angle is being determined. The splines can generate an audible "click" at angular increments as the first component is rotated.

Once the proper anteversion angle has been reached, the interdigitating engagement fixes the two components together. Since the proximal body assembly is rotationally locked together, the stem locator feature and the trial locator feature can be externally referenced to determine a relative angular orientation of the first component relative to the distal stem component indicative of the anteversion rotational angle of the femoral component.

One significant benefit of the present invention is that the true anteversion rotational angle of the femur can be determined and accurately approximated in a final hip replacement implant. Another benefit is that certain implant components of the final implant can be used to perform the trialing procedure so no errors arise due to non-conformity of the trial component relative to the implant component.

Another benefit presented by the invention is that the anteversion angle can be determined without requiring external referencing, such as by x-ray. In addition, the invention eliminates the necessity for performing angular measurements and then duplicating these measurements during the construction of the final implant.

These and other benefits can be discerned from the following written description taken together with the accompanying figures.

DESCRIPTION OF THE FIGURES

FIG. 1 is an exploded view of the components of a modular hip replacement system according to one embodiment of the invention.

FIG. 2 is an enlarged side view of a proximal portion of the distal stem component of the hip replacement system shown in FIG. 1.

FIG. 3 is a side view of the sleeve component of the hip replacement system shown in FIG. 1 shown within a prepared bore in the femur.

DETAILED DESCRIPTION OF THE INVENTION

Figure 4:
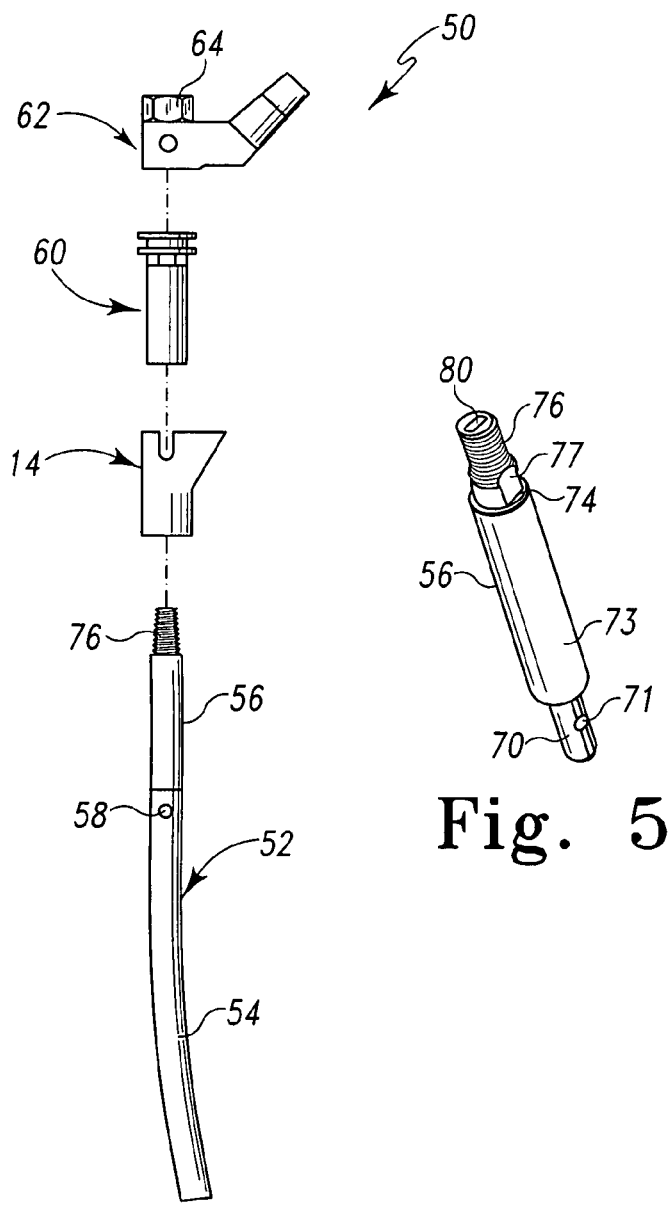
FIG. 4 is an exploded view of the components of a trialing assembly in accordance with one embodiment of the present invention.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

Referring now to FIGS. 1-3, there is shown a modular prosthesis 10 for use during performance of a joint replacement procedure such as a hip replacement procedure. It should be appreciated that although the present invention is herein exemplarily described in regard to performance of a hip replacement procedure, the concepts of the present invention may be utilized in regard to replacement procedures at numerous other joint locations throughout the body. For example, the concepts of the present invention may be utilized in the performance of a shoulder or knee replacement procedure.

The modular femoral prosthesis 10, shown in FIG. 1, includes a proximal component such as a proximal neck component 12, a proximal bone fixation or sleeve component 14, a ball or head component 16, and a distal component such as a distal stem component 18. The prosthesis 10 is configured to be implanted into a femur F (see FIG. 3) of a patient in order to replace certain natural features of the patient's femur F as a result of, for example, disease or trauma. In particular, once assembled in the manner described below, the modular prosthesis 10 is implanted into a surgically prepared (e.g. reamed and/or broached) medullary canal B (see FIG. 3) of the femur F. The modular prosthesis 10 may be press fit into the medullary canal B, or alternatively, may be secured within the medullary canal B by the use of bone cement.

In such a manner, the prosthesis 10 may be utilized to rotatably secure the patient's femur F to the patient's pelvis (not shown). In particular, the head component 16 is positioned to bear on either the patient's natural acetabulum or a prosthetic socket which has been implanted into the patient's pelvis to replace his or her acetabulum. In such a manner, the modular prosthesis 10 and the natural or artificial acetabulum collectively function as a system which replaces the natural "ball and socket" joint of the patient's hip.

As shown in FIG. 1, the distal stem component 18 may be provided in a number of different configurations in order to fit the needs of a given patient's anatomy and provide a variety of fixation options (e.g. textures and geometries) and sizes. In particular, the stem component 18 may be configured in various different lengths in order to conform to the patient's anatomy (e.g. a relatively long stem component 18 for use with a long femur F, a relatively short stem for use with a short femur, etc.). Moreover, the distal stem component 18 may also be provided in a bow-shaped configuration, as depicted in FIG. 1, if required by a given patient's anatomy. Yet further, the distal stem component 18 may also be provided in various diameters and outer textures if required by a given patient's anatomy.

Moreover, it should also be appreciated that, although not shown in FIGS. 1-3, each of the neck component 12, the sleeve component 14, and the head component 16 may also be provided in various differing configurations in order to provide the flexibility necessary to conform to varying anatomies from patient to patient. For example, the head component 16 may be provided in varying diameters or the sleeve component 14 may be provided in varying angles and lengths to fit the needs of a given patient's anatomy. Moreover, both the shape and length of the neck component 26 may also be varied to fit the needs of a given patient's anatomy.

As shown in FIG. 1, the proximal neck component 12 includes a body 20 having a support member or trunnion 22 extending outwardly from a proximal end portion thereof. The head component 16 can be taper fit or otherwise secured to the trunnion 22 in a known manner. The body 20 also has a post 24 extending outwardly from a distal end portion thereof. In the exemplary embodiment shown in FIG. 1, both the trunnion 22 and the post 24 are integrally formed with the body 20 of the proximal neck component 12. However, it should be appreciated that each of these elements may be embodied as separate components which are secured to one another by use of fasteners, press fit joints, or taper fit joints.

In the illustrated embodiment, the sleeve component 14 includes a bore 26 defined therethrough. The bore is sized to receive the post 24 when the modular prosthesis 10 is assembled. The post 24 also includes a bore (not shown) that is sized to receive a post 28 of the distal stem component 18. The distal stem component includes a distal portion 29, which is curved in the illustrated embodiment, but could be straight depending upon the anatomy of the femur F into which the stem 18 is implanted.

Details of one aspect of the present invention can be seen in FIG. 2. More particularly, the invention contemplates certain features on the post 28 of the stem 18. The post 28 can constitute an engagement portion for engaging the neck component 12. In one embodiment, the post includes a tapered shank 32 that is configured for a taper-fit with a complementary configured bore (not shown) in the post 24 of the neck component 12. The stem post 28 terminates in a threaded portion 34 that is configured to engage a nut (not shown) when it is desired to fix the neck component 12 to the stem component 18. Thus far, these elements of the distal stem component are provided to accomplish the final assembly and fixation of the modular implant 10.

Figure 17:
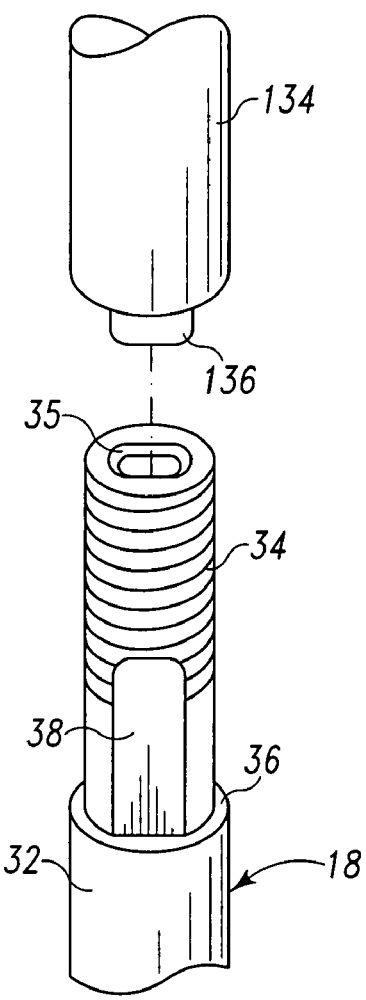
FIG. 17 is a top perspective view of the proximal end of the distal stem component arranged for mating with the locator tip of the alignment instrument shown in FIG. 16.

In accordance with the present invention, the tapered shank 32 defines an annular shoulder 36 adjacent the threaded portion 34. In addition, the threaded portion 34 includes a pair of opposite flats 38. Further, the proximal threaded portion 34 defines a locator feature, such as a locator recess 35 (see FIG. 17) The locator recess 35, shoulder 36 and flats 38 form part of the trialing system of the present invention.

Another aspect of the trialing system is depicted in FIG. 3. In particular, the sleeve component 14 is shown in its position within the prepared bore B in the femur F. It can be seen that a significant portion of the head of the femur is resected to receive the modular implant 10, as well as the trial components described below. The sleeve component includes a pair of oppositely disposed notches 30. These notches 30 are used with the trialing components of the present invention to map the relative rotational alignment of the neck, sleeve and distal stem components relative to an anatomically fixed reference point, such as the intramedullary canal of the femur.

The trialing components are shown in FIGS. 4-14. The exploded view of FIG. 4 shows the basis elements of the trialing system of the present invention. In particular, the trialing assembly 50 includes a trial stem 52 that is formed from a distal stem 54 and a proximal stud 56. The trial stem 52 generally emulates the configuration of the final implant stem, such as stem 18 shown in FIGS. 1-2. However, according to one feature of the invention, the trial stem is a two-piece stem to allow color coding of the distal stem 54. The distal stem of the trial can be provided is a range of lengths, diameters and curvatures. Thus, a number of color-coded distal stems 54 can be supplied. On the other hand, the proximal stud 56 need not be supplied in different sizes. The proximal stud 56 can be engaged to the distal stem 54 by a mating post 70 (FIG. 5) that is configured to be received with a bore 82 (FIG. 6) of the distal stem. A pin 58 (FIGS. 4 and 6) passes through aligned bores 71 (FIG. 5) in the proximal stud 56 and 83 (FIG. 6) in the distal stem 54. Since the trial stem 52 is not intended to be permanently implanted within the patient, this form of connection of the two components is acceptable.

Figure 5:
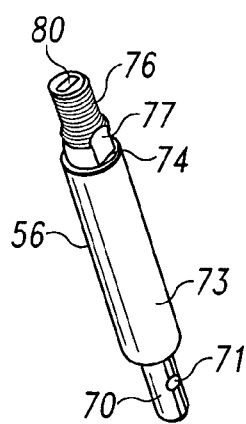
FIG. 5 is an enlarged perspective view of a proximal stud of the trialing assembly shown in FIG. 4.
Figure 6:
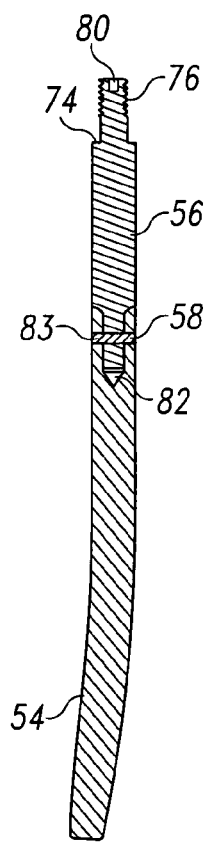
FIG. 6 is a side cross-sectional view of the trial stem of the trialing assembly shown in FIG. 4.
Figure 7:
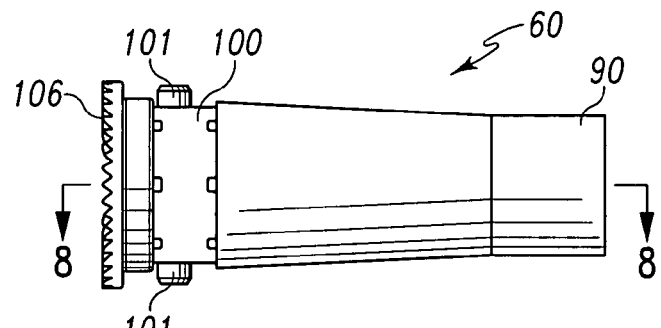
FIG. 7 is a side view of a proximal body assembly of the trialing assembly shown in FIG. 4.

Referring to FIGS. 5 and 6, it can be seen that the proximal end of the proximal stud 56 is configured similar to the proximal end of the distal stem component 18 shown in FIG. 2. In fact, in accordance with the present invention, the trialing procedure can be conducted with the trial stem 52, or with the actual permanent implant distal stem portion 18. In the latter case, the distal stem portion can be selected and firmly fixed within the bore B in the femur F in a known manner.

As with the distal stem portion 18, the proximal stud 56 includes a substantially cylindrical body 73. The body generally corresponds in length to the tapered shank 32 of the distal stem component 18. However, since the trial stem 52 is not permanently implanted, the body 73 need not exhibit the taper-lock configuration of the distal stem component. The proximal stud 56 further includes a threaded portion 76 projecting from the end of the body 73. Like the distal stem component, the body 73 defines an annular shoulder 74 adjacent the threaded portion 76. Further, the threaded portion 76 includes opposite flats 77, similar to the flats 38 of the distal stem component.

The present invention contemplates that the proximal end of the threaded portions, portion 34 of the distal stem component 18 and portion 76 of the proximal stud 56, define a rotational alignment indexing or locator feature, such as recess 35 for the implant stem and recess 80 for the trial stem. In the preferred embodiment, the locator recess is elongated to establish an angular orientation between elements of the trialing assembly 50. Most preferably, the recess 80 (as well as recess 35) is oval, as depicted in FIG. 5. This recess is referenced by an alignment tool, as described herein. In one aspect of the invention, the locator recess 80 is situated at a predetermined angular orientation relative to the distal stem 54 of the trial stem 52 (or the curved portion 29 of the distal stem component 18). This predetermined orientation establishes an external reference that is properly aligned relative to the curvature of the stem so that an accurate anteversion angle can be obtained. In the preferred embodiment, the elongated recess 80 is oriented with its long axis perpendicular to the plane of curvature of the stem. Details of the purpose and use of the locator recess 80 will be explained below, bearing in mind that the features and functions of the recess 80 apply to the recess 35 of the implant distal stem component 18.

Returning to FIG. 4, it can be seen that the trial assembly 50 also incorporates the sleeve component 14. As depicted in FIG. 3, the sleeve component is preferably mounted within the femur F in its implanted position. The sleeve component is preferably not permanently fixed within the bone bore B prior to the trialing process. When the sleeve component 14 is disposed within the femur, the notches 30 are preferably arranged perpendicular to the plane of curvature of the stem. However, the exact rotational relationship of the sleeve component to the distal stem component (or the trial stem) is not critical to the practice of the present invention.

The trialing assembly 50 includes a proximal body assembly 60, which is itself formed of several elements. Details of the proximal body assembly 60 can be discerned from FIGS. 7-11. In particular, the assembly 60 includes a trial body taper component 90, a keyed component 94 (see FIGS. 8 and 10), a proximal ring 100 and a keyed interdigitating component 106. Preferably, the entire completed assembly is provided to a surgeon in a trialing kit, along with the other components of the system.

The taper component 90 is elongated and hollow, having a bore 91 extending therethrough. The proximal end of the bore defines internal threads 92 that engage external threads 96 on the keyed component 94. The bore 91 of the taper component 90 is sized for a loose fit over the proximal stud 56 of the trial stem 52 (or the tapered shank 28 of the stem component 18). The outer surface of the component 90 is tapered to match a portion of the internal taper of the sleeve 14 or of the prepared bore B in absence of a sleeve. The outer diameter of the taper component 90 is further sized to fit through the bore 26 in the sleeve component 14 when the component is mounted within the femoral bore B.

Figure 8:
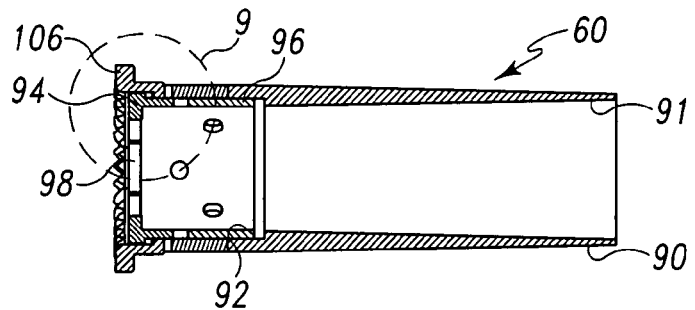
FIG. 8 is an opposite side cross-sectional view of the proximal body assembly shown in FIG. 7, taken along line 8-8 as viewed in the direction of the arrows.

The proximal ring 100 is placed concentrically about the keyed component 94 prior to threading the keyed component 94 external threads 96 into the internal threads 92 of the taper component. The proximal ring 100 is then trapped between the taper component 90 and a flange 97 defined at the proximal end of the taper component, as best shown in FIG. 8 and in the enlarged view of FIG. 9. The proximal ring 100 includes diametrically opposite wings 101 that are configured to be received into the corresponding notches 30 in the sleeve component 14. The wings 101 thus fix the rotational position of the proximal ring 100 relative to the sleeve component.

Figure 9:
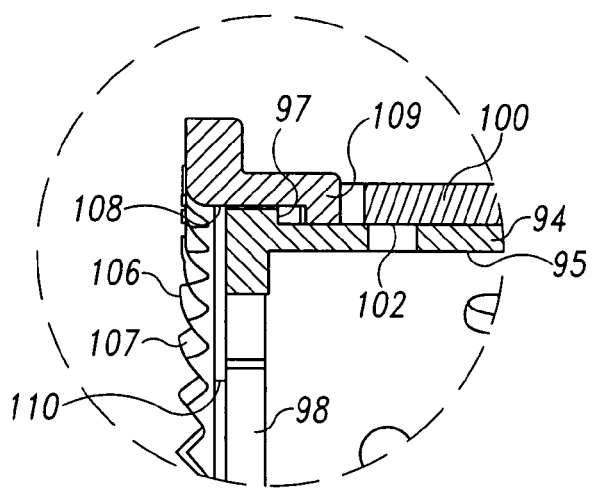
FIG. 9 is an enlarged cross-sectional of the proximal body assembly shown in FIG. 8.
Figure 10:
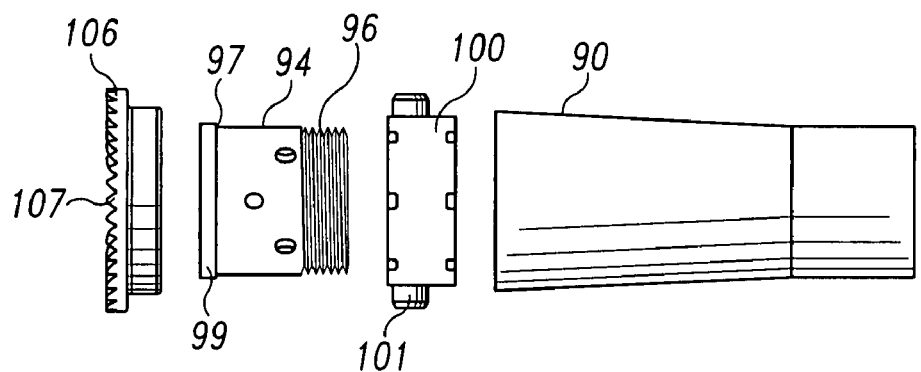
FIG. 10 is an exploded view of the components of the proximal body assembly shown in FIG. 7.
Figure 11:
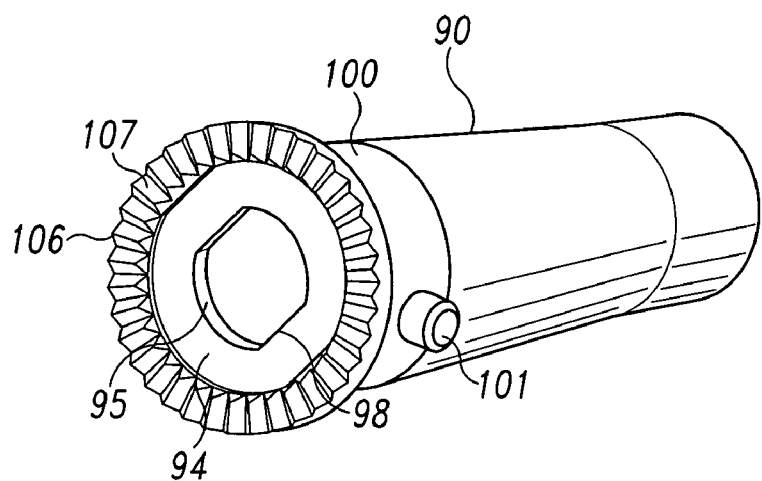
FIG. 11 is a top perspective view of the proximal body assembly shown in FIG. 7.

However, since the keyed component 94 slides within the central bore 102 of the proximal ring, the keyed component (as well as the tapered component 90 in threaded engagement) is free to rotate within the proximal ring. This rotational degree of freedom is important because the keyed component 94 defines internal flats 98 at the flange end of the bore 95, as shown in FIGS. 8, 9 and 11. These internal flats 98 correspond to the flats 38 on the distal stem component 18 and the locator flats 77 on the trial stem 52. The keyed component and the central bore of the proximal ring form a close running fit to eliminate any "slop" between the two components that might lead to an erroneous anteversion angle determination. In other words, the proximal ring 100 supports the keyed component 94 for stable and accurate rotation about the longitudinal axis of the stem component and prepared bore B.

Figure 15:
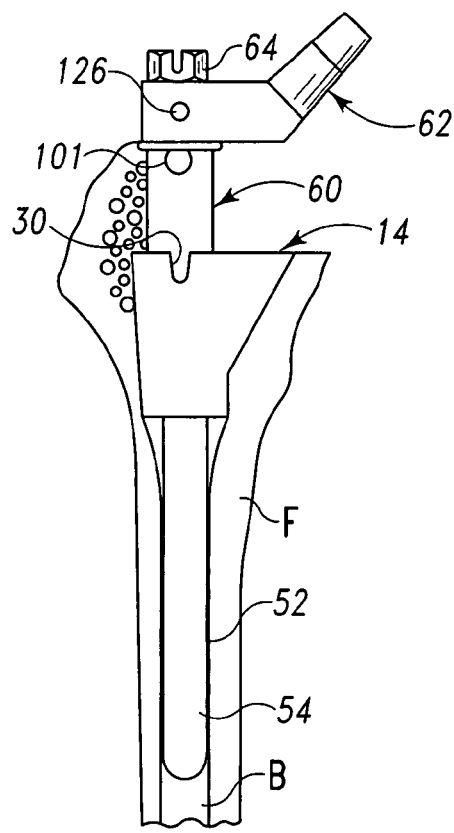
FIG. 15 is a side view of the trial assembly shown in FIG. 4 disposed within the prepared bore in the femur.

When the trialing assembly 50 is engaged within the femur, the trial stem 52 can be situated within the bore B in the femur F. The sleeve component 14 can be disposed within the proximal portion of the bore either before or after the trial stem is positioned. The proximal body assembly 60 can then be placed in position by sliding the trial body taper component 90 through the bore 26 of the sleeve component and around the proximal stud 56 of the trial stem 52 (or around the stem post 28 of the implant component 18), as depicted in FIG. 15. As the taper component is advanced over the proximal stud, the threaded portion 76 passes through the bore 91 of the taper component 90 and the bore 95 of the keyed component 94. Eventually, the keyed component encounters the flats 77 on the threaded portion 76 (or the flats 38 on the implant stem 18). The keyed component is then rotated until the flats 77 (or 38) align with the internal flats 98 of the keyed component. The component is then advanced further over the stem until the keyed component 94 rests on the annular shoulder 74 of the proximal stud 56 (or on the shoulder 36 of the implant). Since the proximal ring 100 is not fixed to either the keyed component 94 or the taper component 90, it can freely rotate relative to the other components so that the wings 101 can be lodged within the notches 30 (see FIG. 15).

These foregoing components provide the foundation for the anteversion rotational alignment capabilities of the present invention. Specifically, the proximal body assembly 60 of the trial assembly 50 includes a keyed interdigitating component 106 that fits over the keyed component 94 in a manner best illustrated in the enlarged view of FIG. 9. As indicated above, the keyed component 94 includes an annular flange 97. The interdigitating component 106 includes a cylindrical body 108 that defines a bore through the component. The distal end of the body 108 is configured as an in-turned flange 109. This in-turned flange 109 is pressed over the flange 97 of the keyed component 94, as shown in FIG. 9, so the interdigitating component 106 is retained on the keyed component. Importantly, the interdigitating component is rotational constrained to the keyed component, meaning that the two components rotate together. In a preferred embodiment, this constraint is accomplished by at least one external flat 99 on the flange 97 of the keyed component 94 and at least one corresponding internal flat 110 defined by the cylindrical body 108 of the interdigitating component 106. Thus, it can be appreciated that the taper component 90, keyed component 94 and interdigitating component 106 rotate together when supported within the sleeve component 14 by the proximal ring 100. Viewed in another way, the ring 100 is free to rotate relative to the other three components of the proximal body assembly 60.

Figure 12:
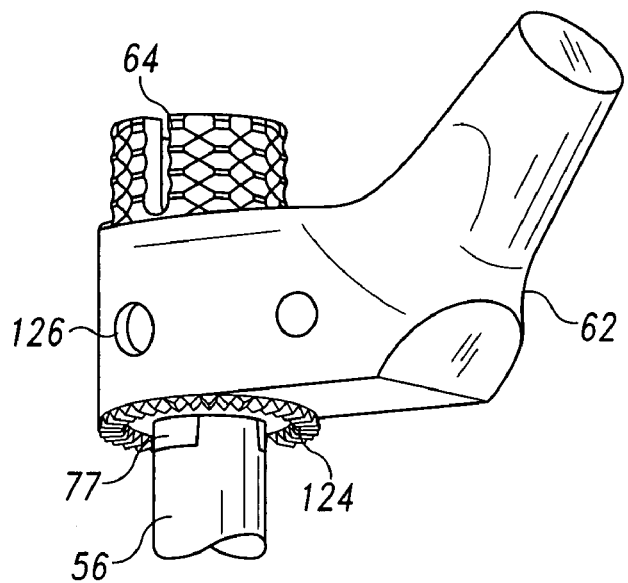
FIG. 12 is a side perspective view of the trial neck component and nut of the proximal body assembly shown in FIG. 4.
Figures 13, 14:
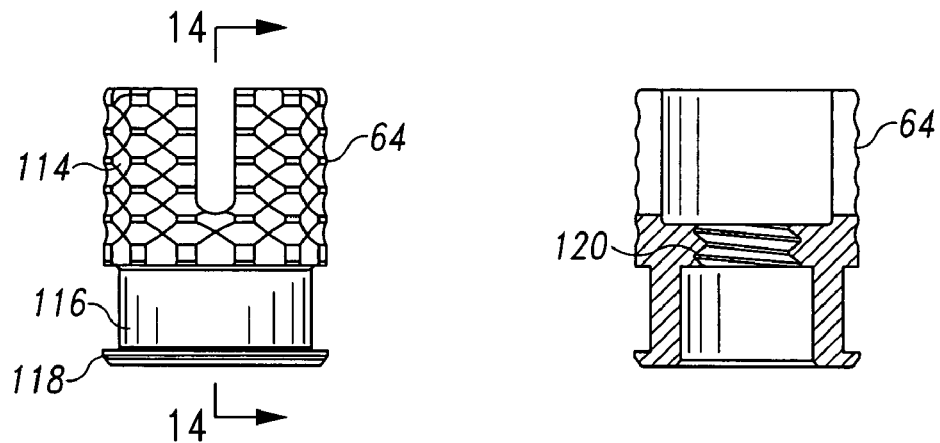
FIG. 13 is a side view of the nut of the proximal body assembly shown in FIG. 7.
FIG. 14 is a cross-sectional view of the nut shown in FIG. 13, taken along line 14-14 as viewed in the direction of the arrows.

The interdigitating component 106 includes a proximally facing toothed surface 107. This surface 107 is configured for interdigitating engagement with a similarly configured surface 124 on the distal face of the trial neck component 62, as shown in FIG. 12. The teeth on both surfaces 107 and 124 can be configured for interdigitation at a predetermined angular interval. For instance, the teeth can allow for relative rotational positioning of the trial neck component 62 relative to the proximal body assembly 60 at ten degree (10°) increments. The interdigitating surfaces 107,124 allow controlled rotation of the trial neck component 62 when the trial assembly 50 is mounted within the femur.

When the proximal body assembly is installed within the sleeve 14 mounted within the bone bore B (as shown in FIG. 15), the threaded portion 76 of the proximal stud 56, or the threaded portion 34 of the implant stem component 18, will extend proximal beyond the interdigitating surface 107 of the component 106. The trial neck component 62 can then be disposed over the exposed threaded portion until the interdigitating surface 124 of the neck component contacts the interdigitating surface 107 of the component 106. The threaded portion 76 or 34 extends freely through a core in the neck component 62 (not shown) so that neck component is free to rotate relative to the stem component 52 or 18, sleeve component 14 and proximal body assembly 60. The surgeon can thus manipulate the relative rotational position of the neck component as necessary to achieve the proper anteversion angle for the particular hip joint.

Once the trial neck component 62 has been properly positioned, the entire trial assembly 50 can be clamped together by way of a nut 64 (FIGS. 4,15). As shown in the detail view of FIGS. 13 and 14, the nut 64 includes internal threads 120 that are configured for threaded engagement with the threaded portions 76 or 34. The nut is provided with a knurled external surface 114 to permit hand tightening of the nut onto the threaded portion. Preferably, the nut 64 is axially captured within the trial neck component 62 while permitting rotation of the nut relative to the component. Thus, the distal end of the nut can include an annular recess 116 and distal retaining flange 118 snap into the bore (not shown) of the trial neck component 62 in a conventional manner. The nut 64 is thus captured with the neck component and can be used to loosely connect the neck component 62 to the trial stem 52 or implant stem component 18. The nut remains loosely threaded onto the threaded portion 76 or 34 while the rotational position of the neck portion 62 is adjusted. Once the proper anteversion angle has been obtained, the nut is tightened onto the threaded portion which clamps the interdigitating surfaces 106,124 together. In addition, tightening the nut also clamps the proximal ring 100 between the tapered component 90 and interdigitating component 106. The nut thus clamps all of the components of the trial assembly 50 together and holds the components at the correct anatomical anteversion rotational angle.

When the anteversion angle has been approximated by the trial assembly 50, an alignment or measurement instrument 130 can be used to evaluate the angular relationship between the trial neck component 62 and the stem component 56 or 18. From one perspective, the trial assembly provides the surgeon with an indication of the orientation of a curved stem, such as implant stem portion 29 or trial stem portion 54, when the stem is mounted within the femur. There is no need to use x-rays to determine the global position of the distal stem component. Significantly, the trial assembly 50 provides a direct indication of the actual anteversion angle of the patient's femur. This direct indication can be simply the clamped rotational position of the assembly components, or can be accurately measured using indicator marks. In the latter case, indicator marks can be provided on the proximal surface of the sleeve component 14 or on a surface of the alignment instrument 130 to visually indicate the rotational orientation of the trial neck component relative to the sleeve component.

Figure 16:
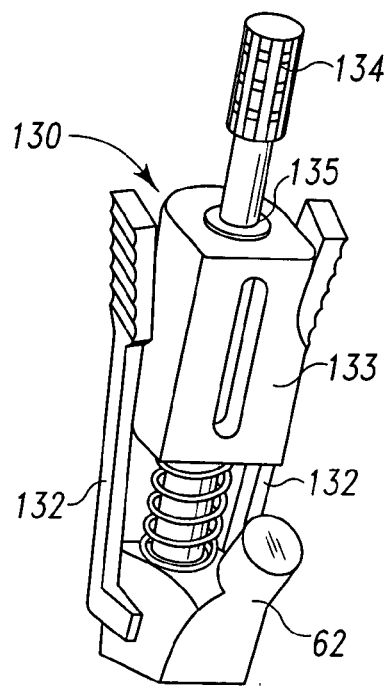
FIG. 16 is a top perspective view of an alignment instrument for use with the trialing system of the present invention.

In one embodiment of the invention, the alignment instrument 130 is used to provide a template for the formation of the final implant, as shown in FIG. 16. The instrument 130 includes a pair of arms 132 that include inward protrusions (not shown) configured to engage indentations or recesses 126 on opposite sides of the trial neck component 62 (see FIGS. 12, 15). The arms are supported on a body 133 so that the distal ends of the arms can be moved apart to receive the neck component therebetween and moved together about the component. The body 133 also supports an alignment shaft 134 that is rotatably disposed within a bore 135. The alignment shaft has a distal end 136 (FIG. 17) that is configured to mate with the locator recess 35 in the end of the implant stem component 18 or the recess 80 in the trial stem component 56. The body 133 can then fix the relative positions of the arms 132 and alignment shaft 134, which then serves as a template for the proper anteversion rotational position of the neck portion relative to the stem portion.

The surgeon can use the instrument 130 to properly locate the implant neck component 12 (FIG. 1) relative to the implant distal stem component 18. The implant neck component 12 can be provided with opposite indentations or recesses 21 that are substantially identical to the recesses 126 on the trial neck component 62 described above. The arms 132 of the alignment instrument 130 can engage these recesses. With the implant neck component 12 essentially supported by the instrument 130, the alignment shaft 134 can be manipulated until its distal end 136 is engaged within the locator recess 35 in the end of the distal stem component 18. Some rotational manipulation of the implant neck component will be necessary until the alignment shaft finds its proper engagement with the locator recess 35. This manipulation is what produces the proper anteversion angle between neck component and distal stem component in the final implant. Once this position has been set by the instrument 130, the instrument can be removed and the final implant components clamped together in conventional fashion. The resulting implant accurately reflects the proper anteversion rotational orientation for the specific patient.

In another embodiment, the alignment instrument 130 can be pre-set to a pre-determined angular position. This angular position can be determined from x-rays of the affected joint to ascertain the actual anteversion angle of the femur. This anteversion angle can then be dialed into the alignment instrument to pre-set the relative orientation between the alignment shaft 134 and the arms 132. The instrument can then be used as explained above to properly position the final implant components, either in situ or at an adjacent preparation table.

In one beneficial aspect of the invention, the implant distal stem component 18 can be used in the trial process. As explained above, the proximal end of the stem component (i.e., the end of the threaded portion 34) includes the locator recess 35 depicted in FIG. 17. In addition, the threaded portion 34 includes opposite flats 38 similar to the flats 77 on the trial proximal stud 56. Thus, in accordance with one method of the invention, the implant distal stem component 18 can be disposed within the bore B in the femur F. Preferably, the stem component is fixed within the bore in a known manner, such as by bone cement. With the implant distal stem component 18 in position within the prepared femur, the sleeve 14 can be added, as shown in FIG. 3. It should be understood that the bore B can be prepared in the femur F in a known manner and that the flared portion of the proximal portion of the bone opening will be dictated by the bone anatomy. Thus, the rotational orientation of the sleeve 14 relative to the curved portion 29 of the distal stem component 18 will vary among patients.

The sleeve component 14 and stem component 18 are part of the final implant 10 shown in FIG. 1. However, the configuration of the threaded portion 34 of the stem component and the provision of the notches 30 in the sleeve component 14 allow these final implant components to be used as part of the trial assembly 50. The proximal body assembly 60, trial neck component 62 and nut 64 can all be used in the manner described above. Thus, the trial stem 52 shown in FIGS. 4 and 15 can be replaced with the implant distal stem component 18 of FIGS. 1 and 2.

Although the proximal end of the distal stem, namely the tapered shank 32, is tapered, the bore 91 of the trial tapered component 90 has a diameter sized to prevent a taper fit between the two components. Thus, the tapered component 90, and consequently the entire proximal body assembly 60, can freely rotate relative to the tapered shank 32 to perform the anteversion rotational alignment functions. The nut 64 is configured to engage the threaded portion 34 of the stem component 18, so the proximal body assembly 60 and trial neck component 62 can be fixed to the sleeve 14 and distal stem component 18. The alignment tool 130 can be used in the manner described above to provide a template for the anteversion rotational angle. The tool 130 can then be used to grab implant neck component 12 and manipulate the component for implantation within the femur. In particular, the tool 130 can carry the neck component 12 to push the post 24 through the bore 26 of the sleeve 14 and about the tapered shank 28. (Note that since the post 24 does not include the wings 101 found on the proximal ring 100, the notches 30 on the sleeve component 14 are no longer needed). As the alignment tool 130 is advanced further, the distal end of the alignment shaft 134 can engage the locator recess 35 in the distal end of the stem component 18. Of course, some rotational manipulation of the tool 130 will likely be needed before the alignment shaft falls into the recess.

When the alignment shaft distal end 136 is properly located in the recess 35, the neck component 12 carried by the tool 130 is situated at the proper anteversion rotational angle. The tool 130 can be readily removed by disengaging the arms 132 from the neck component 12 and sliding the tool upward out of the neck component. The final fixation of the implant components can be accomplished in a known manner, for instance using a tool to pull the tapered components together in a tight taper lock. In a specific embodiment, an implant nut can engage the threaded portion 34 of the distal stem component 18 to act as a secondary locking feature for the implant assembly.

In a preferred embodiment of the invention, the components of the modular prosthesis 10 can be configured as disclosed in commonly-owned, co-pending patent applications Ser. No. 10/033,105, filed on Oct. 22, 2001, and entitled "Modular Prosthesis Having a Stem Component with a Counterbored Cavity Defined Therein and Associated Method" (the '105 Application), and Ser. No. 10/032,984, filed on Oct. 23, 2001 and entitled "Self-Locking Modular Prosthesis Having Taper Feature and Associated Method". The disclosures of both co-pending applications are incorporated herein by reference, and particularly FIGS. 6-12 and the associated descriptive text. It should be understood that the details of the implant components and their manner of fixation can be readily ascertained from the disclosures of the '105 and '984 Applications incorporated herein by reference. It should also be understood that while the '105 and '984 Applications depict a straight distal stem component, the same "self-locking" features can be implemented with a curved stem, such as the curved distal stem component 18 of the present invention. However, the present invention contemplates modifications to the distal stem component that allow the implant components to be incorporated into the trial assembly 50 as described above. Moreover, the concepts of the present invention can be incorporated into a modular prosthesis that does not implement the self-locking features described in the referenced co-pending applications.

The modular implant of the present invention forms part of a trial assembly 50 as described above. Certain details of the trial assembly, including the trial stem 52, the proximal body assembly 60 and the trial neck component 62, is the subject of commonly-owned, U.S. application Ser. No. 10/327,527, filed on Dec. 20, 2002, which description is incorporated herein by reference. Likewise, details of the alignment instrument 130 described above is the subject of commonly-owned, U.S. application Ser. No. 10/327,196, filed on Dec. 20, 2002 (now U.S. Pat. No. 7,022,141), which description is also incorporated herein by reference. Certain aspects of the subject matter of these two commonly-owned co-pending applications has been described to assist in understanding the present invention. It should be understood that certain details of the aforementioned components have been left to these co-pending applications.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected. For example, the preferred embodiment of the invention contemplates the provision of a locator recess 35 in the implant distal stem component 18 and the recess 80 in the trial stem 52. However, the recess can instead constitute a locator feature that is externally accessible by an instrument, such as the alignment instrument 130, to determine the rotational position of the distal stem component within the prepared bore B of the femur F. For instance, the recess can be replaced with an elongated upwardly projecting boss, with appropriate modification to the alignment shaft 134 of the instrument 130. Moreover, the locating feature can be in the form of a key-shaped slot in the proximal portion of the implant or trial stems, where the slot is either fully contained within the end surface of extends through the side surface of the proximal portion.

Figure 18:
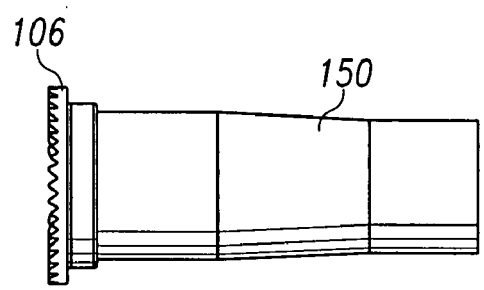
FIG. 18 is a side view of an alternative proximal body assembly that may be used in the trialing assembly of the present invention.

In another modification, the trial proximal body component can be modified where no implant sleeve component is used in the final replacement hip system. In other words, with some hip systems, the sleeve component 14 and the neck component 12 is modified accordingly. In this case, the trial proximal body assembly does not require the proximal ring 100 or the wings 101. In this instance, the trial proximal body assembly can be configured as shown in FIG. 18 which includes only a modified trial body taper component 150 and the keyed interdigitating component 106. The component 150 can have a distal portion configured like the component 90 described above. The proximal end of the component can be extended to account for the height of the unused proximal ring. In addition, the proximal end of the extended trial body taper component 150 is configured like the proximal end of the keyed component 94, which is also unnecessary with the modified assembly. In other words, the internal flats 98 shown in FIG. 9 are incorporated into the proximal end of the trial body taper component 150. Likewise, the proximal end can include the external flange 97 used to engage the inturned flange 109 of the interdigitating component 106 (see FIG. 9).

What is claimed is:

1. A trialing system for use with a modular hip replacement system, comprising:
    a stem component configured to be fixed within a prepared bone, the stem component including a proximal portion defining a longitudinal axis and defining a stem locator feature indicative of an orientation of the stem component with respect to the longitudinal axis;
    a keyed trial component configured to engage the proximal portion in a keyed relationship while allowing access to the stem locator feature; and
    a trial neck component including a trial locator feature and engageable with the proximal portion and matable with the keyed trial component at a plurality of angles in a plane perpendicular to the longitudinal axis, such that when the keyed trial component is keyedly engaged with the proximal portion, the trial neck component can be i) engaged with the proximal portion, ii) rotated to a selected one of the plurality of angles with respect to the keyed trial component, and iii) mated to the keyed trial component, while allowing access to the stem locator feature and to the trial locator feature;
    wherein the keyed trial component includes a discrete first plurality of splines at a proximal end thereof, said discrete first plurality of splines configured to extend perpendicularly to the longitudinal axis when the keyed trial component is engaged with the proximal portion; and the trial neck component includes a second plurality of splines, the second plurality of splines formed complementary to the first plurality of splines; and
    wherein the keyed trial component comprises a first bore with a first diameter, the first bore extending from a distal end of the keyed trial component to a proximal end of the keyed trial component; the proximal portion comprises an elongated portion extending proximally from a widened portion, the elongated portion sized to extend through the first bore, and the widened portion including a dimension wider than the first diameter; and the stem locator feature is located on the elongated portion such that when the keyed trial component is engaged with the proximal portion, the stem locator feature is located proximal to the proximal end of the keyed trial component alone the longitudinal axis.

2. The trialing system of claim 1, wherein the trial neck component comprises:
    a second bore with a second diameter, the second bore extending from a distal end of the trial neck component to a proximal end of the trial neck component, the second bore sized to receive the elongated portion such that when the keyed trial component is engaged with the proximal portion and the trial neck component is engaged with the proximal portion, the stem locator feature is accessible through the second bore.

3. The trialing system of claim 2, wherein:
    the proximal end of the keyed trial component defines a first plurality of splines configured to extend perpendicularly to the longitudinal axis when the keyed trial component is engaged with the proximal portion; and
    the distal end of the trial neck component defines a second plurality of splines, the second plurality of splines formed complementary to the first plurality of splines.

4. The trialing system of claim 1, wherein:
    the stem component comprises a distal portion curved in a plane of curvature; and
    the stem locator feature is oriented at a predetermined angle relative to the plane of curvature.

5. The trialing system of claim 4, wherein the stem locator feature is a recess.

6. The trialing system of claim 5, wherein the stem locator feature defines an ovoid in a plane perpendicular to the longitudinal axis.

7. A trialing system for use with a modular hip replacement system, comprising:
    a stem component configured to be fixed within a prepared bone, the stem component including a proximal portion with a ledge and an elongated portion extending proximally from the ledge, the elongated portion defining a longitudinal axis and defining a stem locator feature;
    a keyed trial component configured to be positioned upon the ledge in a keyed relationship with the proximal portion; and
    a trial neck component including a trial locator feature and engageable with the elongated portion and matable with the keyed trial component at a plurality of angles in a plane perpendicular to the longitudinal axis, such that when the keyed trial component is keyedly engaged with the elongated portion, the trial neck component can be i) engaged with the elongated portion, ii) rotated to a selected one of the plurality of angles with respect to the keyed trial component, and iii) mated to the keyed trial component, while allowing access to the stem locator feature and to the trial locator feature;
    wherein the keyed trial component comprises a first bore with ledge; the bore ledge is configured to be positioned on the stem ledge; the first bore extends proximally from the bore ledge to a proximal end of the keyed trial component; and the height of the first bore from the bore ledge to the proximal end of the keyed trial component is less than the length of the elongated portion alone the longitudinal axis, such that when the keyed trial component is positioned on the ledge, the stem locator feature is located proximal to the proximal end of the keyed trial component along the longitudinal axis; and wherein the proximal end of the keyed trial component defines a discrete first plurality of splines configured to extend perpendicularly to the longitudinal axis when the keyed trial component is engaged with the proximal portion; and a distal end of the trial neck component defines a second plurality of splines, the second plurality of splines formed complementary to the first plurality of splines.

8. The trialing system of claim 7, wherein the trial neck component comprises:

a second bore extending from a distal end of the trial neck component to a proximal end of the trial neck component, the second bore sized to receive the elongated portion such that when the keyed trial component is positioned on the ledge, the stem locator feature is accessible through the second bore.

9. The trialing system of claim 7, wherein:

the stem component comprises a distal portion curved in a plane of curvature; and the stem locator feature is oriented at a predetermined angle relative to the plane of curvature.

10. The trialing system of claim 7, wherein the stem locator feature defines an ovoid in a plane perpendicular to the longitudinal axis.

11. A trialing system for use with a modular hip replacement system, comprising:

a stem component configured to be fixed within a prepared bone, the stem component including a proximal portion with an elongated portion and a keyed portion, the elongated portion defining a longitudinal axis and defining a stem locator feature;

a keyed trial component configured to be mated with the keyed portion in a keyed relationship with the proximal portion; and a trial neck component including a trial locator feature and engageable with the elongated portion and matable with the keyed trial component at a plurality of angles in a plane perpendicular to the longitudinal axis, such that when the keyed trial component is keyedly engaged with the elongated portion, the trial neck component can be i) engaged with the elongated portion, ii) rotated to a selected one of the plurality of angles with respect to the keyed trial component, and iii) mated to the keyed trial component, while allowing access to the stem locator feature and to the trial locator feature;

wherein the elongated portion extends proximally from an enlarged portion; the keyed trial component comprises a first bore; the first bore extends from a distal end of the keyed trial component to a proximal end of the keyed trial component and includes an internal ledge; the diameter of the first bore distal to the internal ledge is greater than the diameter of the enlarged portion; and the diameter of the first bore proximal to the internal ledge is less than the diameter of the enlarged portion and greater than the diameter of the elongated; and wherein the proximal end of the keyed trial component defines a discrete first plurality of splines configured to extend perpendicularly to the longitudinal axis when the keyed trial component is engaged with the proximal portion; and a distal end of the trial neck component defines a second plurality of splines, the second plurality of splines formed complementary to the first plurality of splines.

12. The trialing system of claim 11, wherein:

the elongated portion defines a generally cylindrical periphery about the longitudinal axis; and the keyed portion comprises a flat area of the generally cylindrical periphery.

13. The trialing system of claim 11, wherein the trial neck component comprises:

a second bore extending from a distal end of the trial neck component to a proximal end of the trial neck component, the second bore sized to receive the elongated portion such that when the keyed trial component is mated with the keyed portion and the trial neck component is engaged with the proximal portion, the stem locator feature is accessible through the second bore.

14. The trialing system of claim 13, wherein:

the stem component comprises a distal portion curved in a plane of curvature; and the stem locator feature is oriented parallel to the plane of curvature.

15. The trialing system of claim 14, wherein the stem locator feature defines an ovoid in a plane perpendicular to the longitudinal axis.

* * * * *